US008926661B2

(12) United States Patent
Sikora et al.

(10) Patent No.: US 8,926,661 B2
(45) Date of Patent: Jan. 6, 2015

(54) SURGICAL FASTENING

(75) Inventors: George J. Sikora, Bridgewater, MA (US); James J. Sullivan, Shrewsbury, MA (US); Pascal Boileau, Nice (FR); Stephen Anthony Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 63 days.

(21) Appl. No.: 13/213,966

(22) Filed: Aug. 19, 2011

(65) Prior Publication Data
US 2012/0310279 A1  Dec. 6, 2012

Related U.S. Application Data

(60) Provisional application No. 61/492,497, filed on Jun. 2, 2011, provisional application No. 61/492,484, filed on Jun. 2, 2011.

(51) Int. Cl.
*A61B 17/04* (2006.01)
*A61B 17/68* (2006.01)

(52) U.S. Cl.
CPC ..... *A61B 17/0401* (2013.01); *A61B 2017/0414* (2013.01); *A61B 17/683* (2013.01); *A61B 2017/0404* (2013.01); *A61B 2017/0419* (2013.01); *A61B 17/0485* (2013.01)
USPC ........................................... 606/232; 606/60

(58) Field of Classification Search
USPC ........... 606/60, 148, 228, 232, 280, 281, 286, 606/300; 623/13.11, 13.14, 19.11, 19.13, 623/19.14; 128/898
See application file for complete search history.

(56) References Cited

U.S. PATENT DOCUMENTS

| 3,896,500 A | 7/1975 | Rambert et al. |
| 3,910,281 A | 10/1975 | Kletschka et al. |

(Continued)

FOREIGN PATENT DOCUMENTS

| EP | 2238944 A3 | 3/2012 |
| FR | 2815843 A1 | 5/2002 |

OTHER PUBLICATIONS

Struhl, Steven, "Double Endobutton Technique for Repair of Complete Acromioclavicular Joint Dislocations," Techniques in Shoulder and Elbow Surgery, vol. 8, Issue 4, pp. 175-179, 2007.

(Continued)

*Primary Examiner* — Dianne Dornbusch
*Assistant Examiner* — Robert Lynch
(74) *Attorney, Agent, or Firm* — Burns & Levinson LLP; Joseph M. Maraia; Michael A. Mattoni

(57) ABSTRACT

A surgical device includes a first fastener having a planar profile, a second fastener having a concave surface, and a suture that can be manipulated to change a distance between the first and second fasteners. The second fastener has a curvature that substantially matches the curvature of a top surface of a clavicle bone in a direction perpendicular to a long axis of the clavicle bone. A method of treating an acromioclavicular joint injury includes forming axially aligned passages through a patient's clavicle and coracoid process, passing a fastener having a concave surface through the passages, positioning the concave surface of the fastener against a top surface of the patient's clavicle with a long axis of the fastener extending perpendicular to a long axis of the clavicle, positioning a fastener having a planar profile below the patient's coracoid process, and adjusting a suture that couples the fasteners.

20 Claims, 17 Drawing Sheets

(56) References Cited

U.S. PATENT DOCUMENTS

| | | | |
|---|---|---|---|
| 5,306,290 | A | 4/1994 | Martins et al. |
| 5,306,301 | A | 4/1994 | Graf et al. |
| 6,063,106 | A | 5/2000 | Gibson |
| 6,149,669 | A * | 11/2000 | Li .............................. 606/232 |
| 6,514,274 | B1 | 2/2003 | Boucher et al. |
| 7,235,091 | B2 | 6/2007 | Thornes |
| 7,500,983 | B1 | 3/2009 | Kaiser et al. |
| 7,572,275 | B2 | 8/2009 | Fallin et al. |
| 8,162,997 | B2 | 4/2012 | Struhl |
| 2002/0161439 | A1 | 10/2002 | Strobel et al. |
| 2002/0173788 | A1 | 11/2002 | Bojarski et al. |
| 2005/0192632 | A1 | 9/2005 | Geissler et al. |
| 2005/0277961 | A1 | 12/2005 | Stone et al. |
| 2006/0190041 | A1 | 8/2006 | Fallin et al. |
| 2006/0241619 | A1 | 10/2006 | Cerundolo |
| 2007/0016208 | A1 | 1/2007 | Thornes |
| 2007/0150002 | A1 | 6/2007 | Szabo et al. |
| 2007/0179531 | A1 | 8/2007 | Thornes |
| 2007/0270804 | A1 | 11/2007 | Chudik |
| 2008/0177302 | A1 | 7/2008 | Shurnas |
| 2008/0208252 | A1 | 8/2008 | Holmes |
| 2008/0312689 | A1 | 12/2008 | Denham et al. |
| 2009/0054928 | A1 | 2/2009 | Denham et al. |
| 2009/0182335 | A1 | 7/2009 | Struhl |
| 2009/0318923 | A1* | 12/2009 | Burkhart et al. ................ 606/87 |
| 2010/0069926 | A1 | 3/2010 | Goble et al. |
| 2010/0125297 | A1 | 5/2010 | Guederian et al. |
| 2010/0211075 | A1 | 8/2010 | Stone |
| 2011/0087280 | A1* | 4/2011 | Albertorio .................. 606/232 |
| 2011/0137341 | A1 | 6/2011 | Thornes et al. |
| 2012/0150203 | A1 | 6/2012 | Brady et al. |
| 2012/0253352 | A1 | 10/2012 | Smith |

OTHER PUBLICATIONS

"AC Joint TightRope Fixation: Arthroscopic Stabilization of Acute Acromioclavicular Joint Disclocation Using the TightRope System, Surgical Technique," Arthrex Inc., 2007, 6 pages.

Petersen, W., et al., "Minimally Invasive Acromioclavicular Joint Reconstruction (MINAR)," Abstract, Oper Orthop Tramatol. Mar. 2010; 22(1):52-61, 1 page.

Petersen, W., et al., "Minimal Invasive AC Joint-Reconstruction (MINAR)," EndoWorld OSM 35-E/01-2008, Karl Storz—Sports Medicine, Inc., 2008, 9 pages.

"MINAR-Set—Minimal Invasive Reconstruction of the Acromioclavicular Joint," Karl Storz Endoskope—MINAR-Set, reprinted from http://www.karlstorz.com/cps/rde/xchg/SID-07F49210-20462E33/karlstorz-en/hs.xsl/9117 on Jun. 16, 2010, 1 page.

Boileau, P., et al., "All-Arthroscopic Weaver-Dunn-Chuinard Procedure with Double-Button Fixation for Chronic Acromioclavicular Joint Disclocation," The Journal of Arthroscopic and Related Surgery, vol. 26, No. 2 Feb. 2010, pp. 149-160.

Wellmann, M., et al., Minimally Invasive Coracoclavicular Ligament Augmentation with a Flip Button/Polydioxanone Repair for Treatment of Total Acromioclavicular Joint Disclocation, The Journal of Arthroscopic and Related Surgery, vol. 23, No. 10 Oct. 2007, pp. 1132.e1-1132.e5.

International Search Report and Written Opinion for International Application No. PCT/US2012/040538, mailed Oct. 8, 2012, pp. 1-25.

* cited by examiner

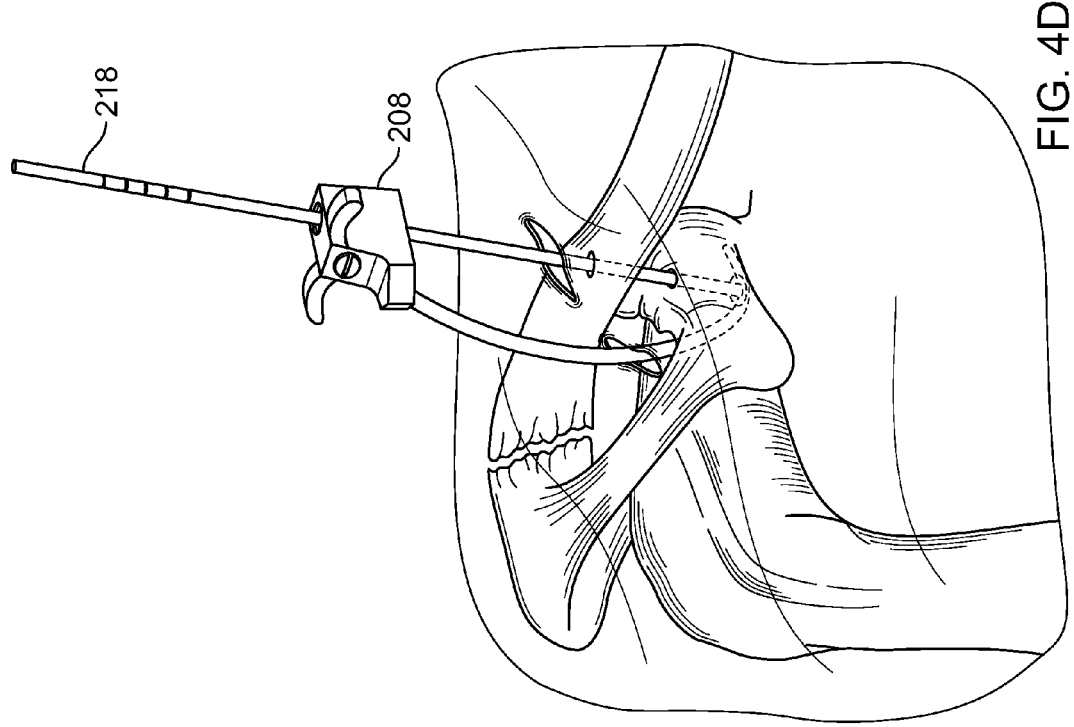
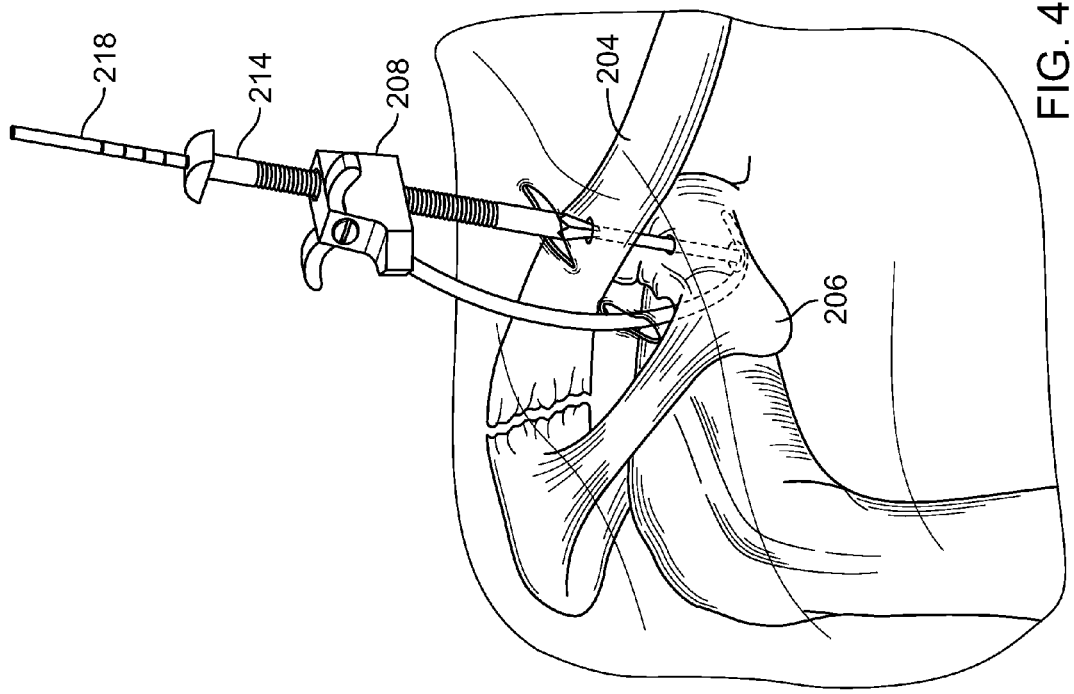

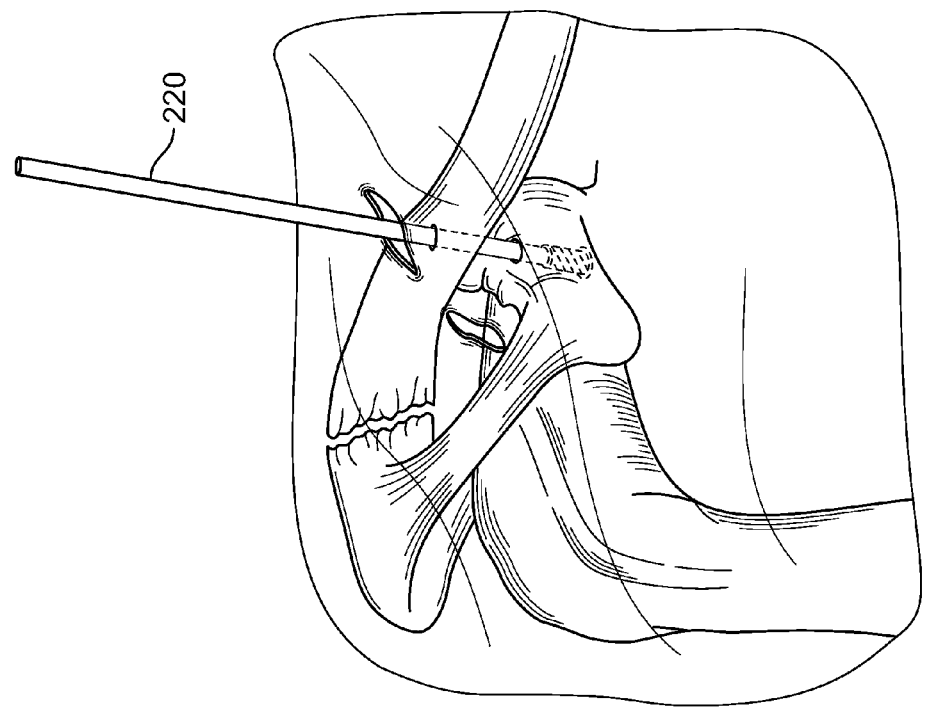
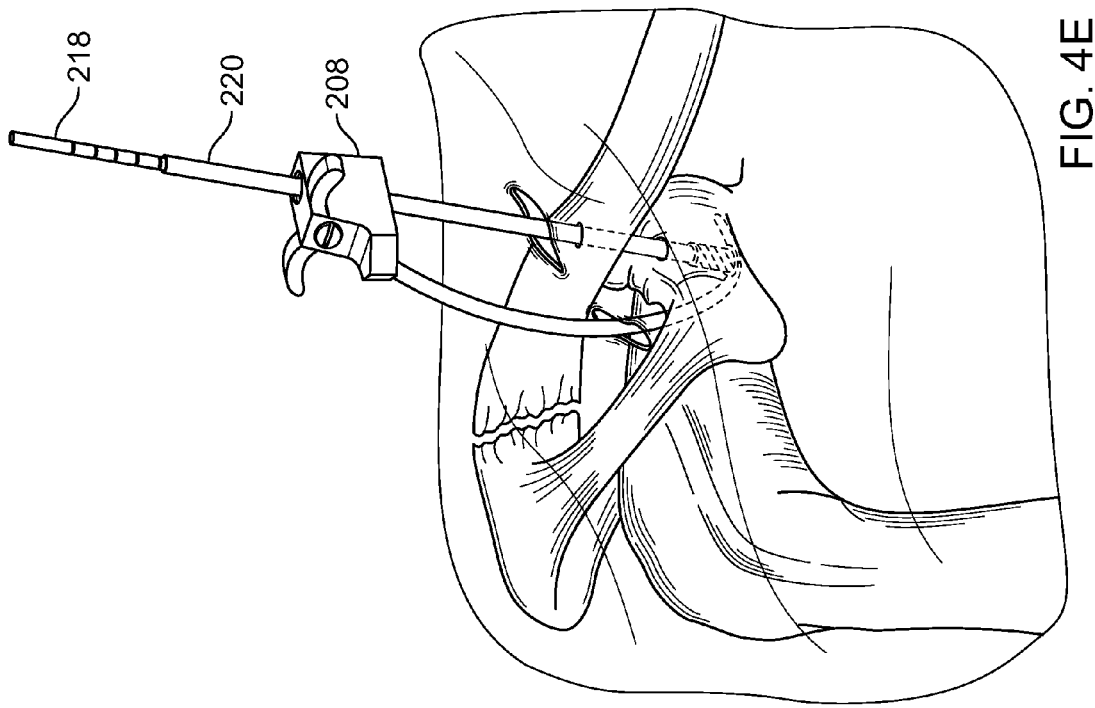

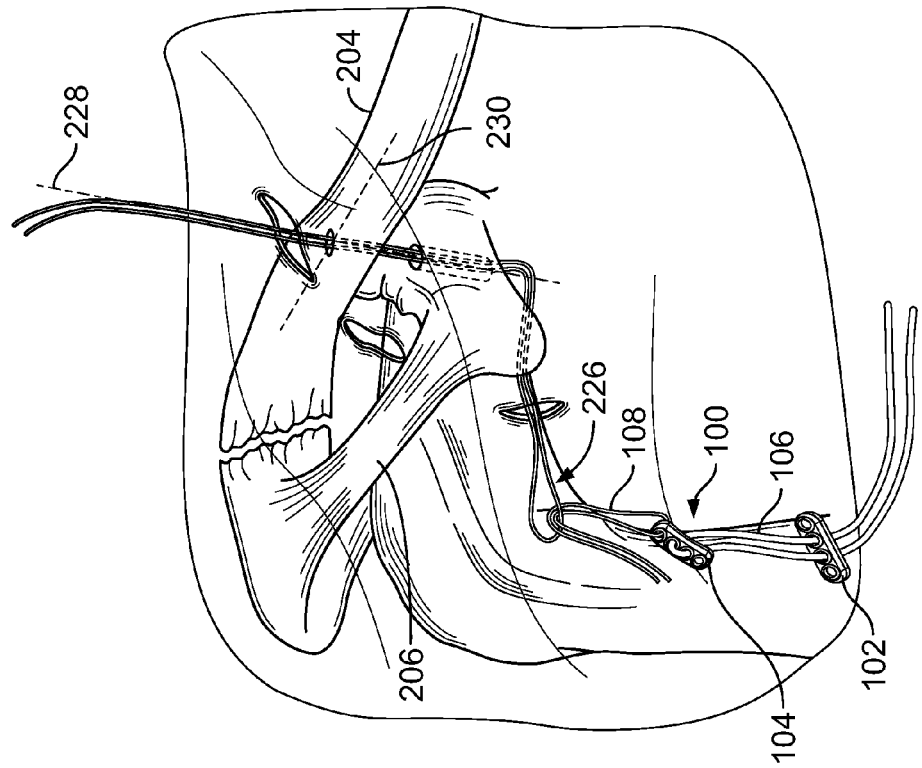
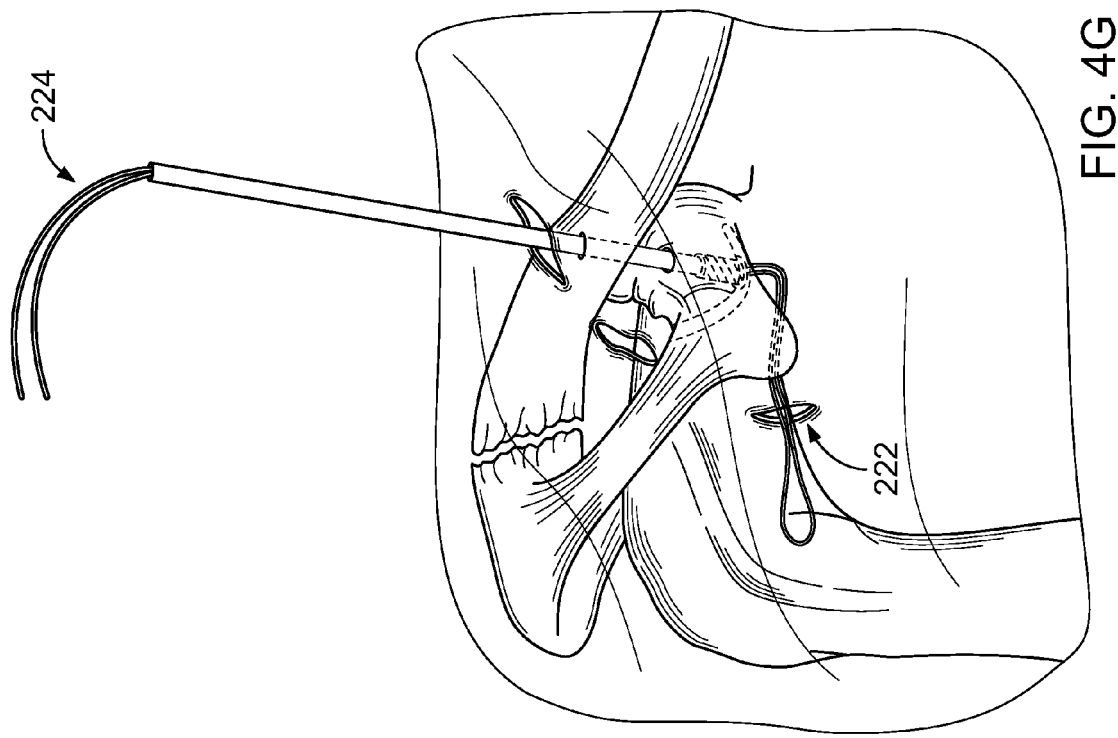
FIG. 4G
FIG. 4H

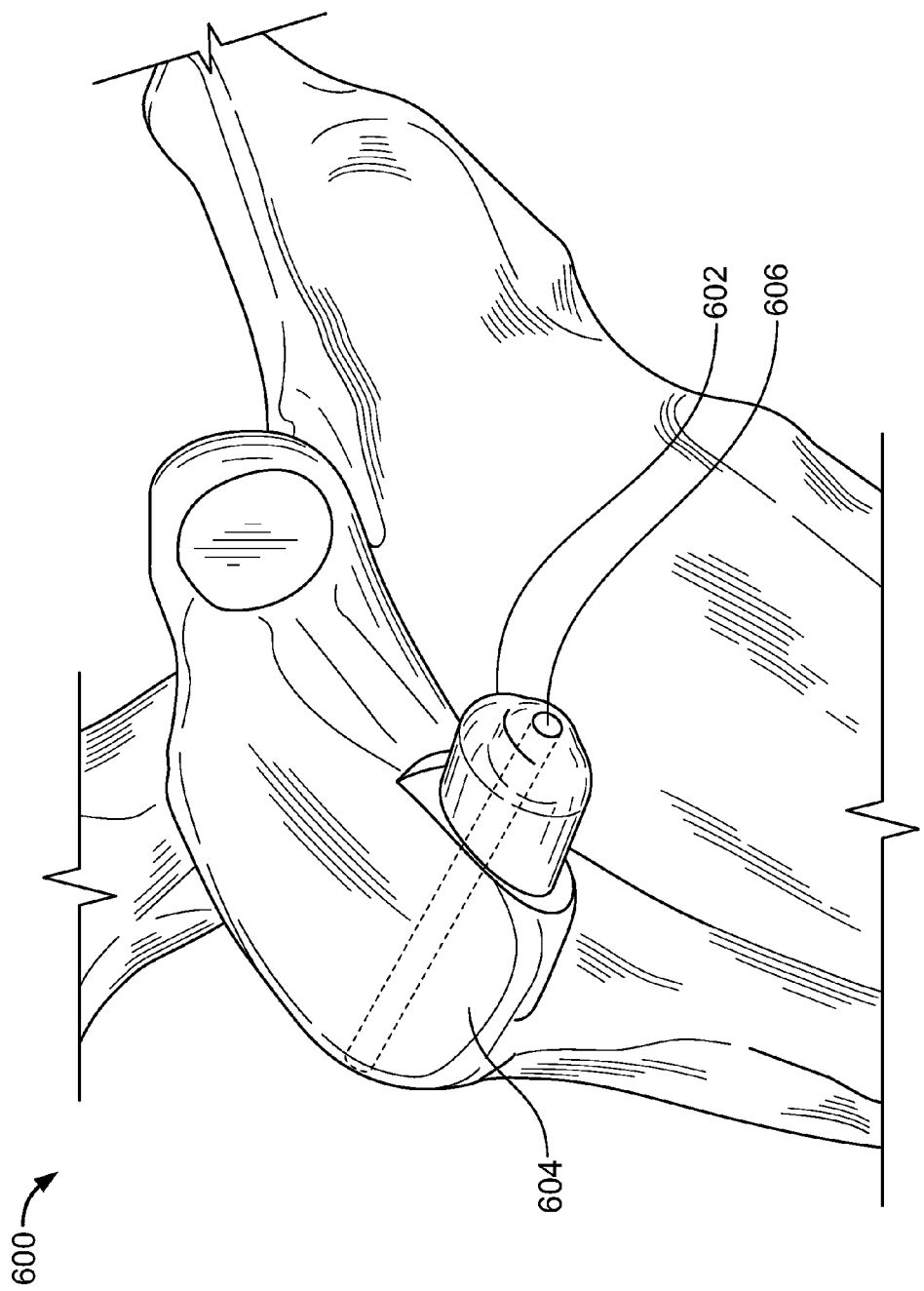

SURGICAL FASTENING

CROSS-REFERENCE TO RELATED APPLICATIONS

This application claims the benefit of priority from U.S. Provisional Application Ser. No. 61/492,497, filed Jun. 2, 2011, and titled DOUBLE ENDOBUTTON AND DELIVERY DEVICE, and from U.S. Provisional Application Ser. No. 61/492,484, filed Jun. 2, 2011, and titled DOUBLE BUTTON CONSTRUCT FOR LATARJET REPAIR.

TECHNICAL FIELD

This description relates to surgical fastening.

BACKGROUND

Joint and ligament injuries are common. One type of such injuries includes acromioclavicular joint and coracoclavicular tendon disruptions. In treating these various joint and tendon injuries, it has been common to utilize woven polyester slings or surgical screws. The goal of any such treatment is to re-approximate bones, tendons and ligaments back to their anatomical locations to facilitate the healing process.

SUMMARY

According to one aspect, a surgical fastening device includes a first fastener having a planar profile, a second fastener having a curvature along a longitudinal axis of the second fastener, a length of the second fastener along the longitudinal axis being greater than a width of the second fastener along a lateral axis of the second fastener, and a suture coupled to the first and second fasteners such that the suture is able to be manipulated to change a distance between the first and second fasteners.

Embodiments of this aspect may include one or more of the following features.

Each fastener defines at least two holes for receiving the suture. The first fastener includes a least a third hole for receiving a second suture. The suture is tied in a half-hitch. The half-hitch is located against an outer surface of the first fastener. The fasteners are generally rectangular in shape. The second fastener is configured to have a curvature that substantially matches the curvature of a top surface of a human clavicle bone in a direction perpendicular to a long axis of the human clavicle bone.

According to another aspect, a method of treating an acromioclavicular (AC) joint injury includes forming axially aligned passages through a patient's clavicle and coracoid process, passing a fastener having a concave surface through the passages, positioning the concave surface of the fastener against a top surface of the patient's clavicle with a long axis of the fastener extending perpendicular to a long axis of the clavicle, positioning a fastener having a planar profile below the patient's coracoid process, and adjusting a suture that couples the fasteners to decrease a distance between the fasteners.

Embodiments of this aspect may include one or more of the following features.

The suture includes a half-hitch knot and adjusting the suture includes pulling on ends of the suture. The method includes tying a knot in the suture such that the knot is against an outer surface of the planar fastener. Passing the fastener having a concave surface through the passages includes pulling on a second suture attached to the concave fastener.

According to another aspect, a method includes positioning a bone graft in contact with a patient's glenoid, forming at least one axially aligned passage through the patient's glenoid and the bone graft, passing a first portion of the suture through the passage, wherein a second portion of the suture is coupled to a first fastener, positioning a surface of the first fastener against a surface of the bone graft opposite a surface of the bone graft in contact with the patient's glenoid, positioning a surface of a second fastener against a surface of the glenoid opposite a surface of the gelnoid in contact with the bone graft, wherein the second fastener is coupled to a third portion of the suture, and adjusting the suture such that the first fastener and the second fastener apply pressure between the bone graft and the patient's glenoid.

Embodiments of this aspect may include one or more of the following features.

The bone graft is at least a portion of the patient's coracoid process. Positioning the portion of the patient's coracoid process in contact with the patient's glenoid includes positioning the portion of the patient's coracoid process upright such that a longest dimension of the patient's coracoid process is oriented substantially orthogonal to the surface of the gelnoid in contact with the patient's coracoid process. Positioning the portion of the patient's coracoid process in contact with the patient's glenoid includes positioning the portion of the patient's coracoid process laying down such that a longest dimension of the patient's coracoid process is oriented substantially parallel to the surface of the gelnoid in contact with the patient's coracoid process. The first fastener and the second fastener each have a planar profile. The first fastener has a planar profile and the second fastener has a curvature along a longitudinal axis of the second fastener, a length of the second fastener along the longitudinal axis being greater than a width of the second fastener along a lateral axis of the second fastener. The second fastener further has a curvature along a lateral axis of the second fastener. The second fastener has a circular body with a convex surface and a corresponding, opposite concave surface. The second fastener defines two holes for receiving suture and a neck protruding from the concave surface that surrounds the two holes, an outer diameter of the neck being less than or equal to a diameter of the passage through the bone graft.

According to another aspect, a method includes positioning a bone graft in contact with a patient's glenoid, forming two axially aligned passages through the patient's glenoid and the bone graft, inserting a bone anchor into each of the two passages in the patient's glenoid, wherein each bone anchor includes a length of suture that protrudes from the patient's glenoid when the bone anchor is inserted, passing a first portion of suture attached to a first of the bone anchors through a first passage in the bone graft, passing a second portion of suture attached to a second of the bone anchors through a second passage in the bone graft, positioning a surface of a first fastener against a surface of the bone graft opposite a surface of the glenoid in contact with the bone graft, wherein the first fastener is coupled to the first portion of suture and the second portion of suture, and adjusting the suture such that the first fastener applies pressure between the bone graft and the patient's glenoid.

Embodiments of this aspect may include one or more of the following features.

The first fastener has a curvature along a longitudinal axis of the second fastener and a curvature along a lateral axis of the second fastener, a length of the second fastener along the longitudinal axis being greater than a width of the second fastener along a lateral axis of the second fastener. A third portion of suture is attached to the first bone anchor and the first fastener, a fourth portion of suture is attached to the second bone anchor and the first fastener, and the first, second, third, and fourth portions of suture are tied together to form a half-hitch knot.

According to another aspect, a surgical fastening device includes a first fastener having a concave surface, a first and a second bone anchor, and a first suture coupled to the first bone anchor and the first fastener and a second suture coupled to the second bone anchor and the first fastener such that the first and second sutures are able to be manipulated to change a distance between the first fastener and the first and second bone anchors.

Embodiments of this aspect may include one or more of the following features.

The first fastener has a curvature along a longitudinal axis of the second fastener and a curvature along a lateral axis of the second fastener, a length of the second fastener along the longitudinal axis being greater than a width of the second fastener along a lateral axis of the second fastener. A third suture is coupled to the first bone anchor and the first fastener, a fourth suture is coupled to the second bone anchor and the first fastener, and the first, second, third, and fourth portions of suture are tied together to form a half-hitch knot.

The details of one or more embodiments are set forth in the accompanying drawings and the description below. Other features, objects, and advantages will be apparent from the description and drawings, and from the claims.

DESCRIPTION OF DRAWINGS

FIGS. 4A-4I illustrate a process for using the surgical fastening device of FIG. 1.

FIGS. 6A-6E illustrate an alternate process for using the surgical fastening device of FIG. 1.

Like reference symbols in the various drawings indicate like elements.

DETAILED DESCRIPTION

Figure 1:
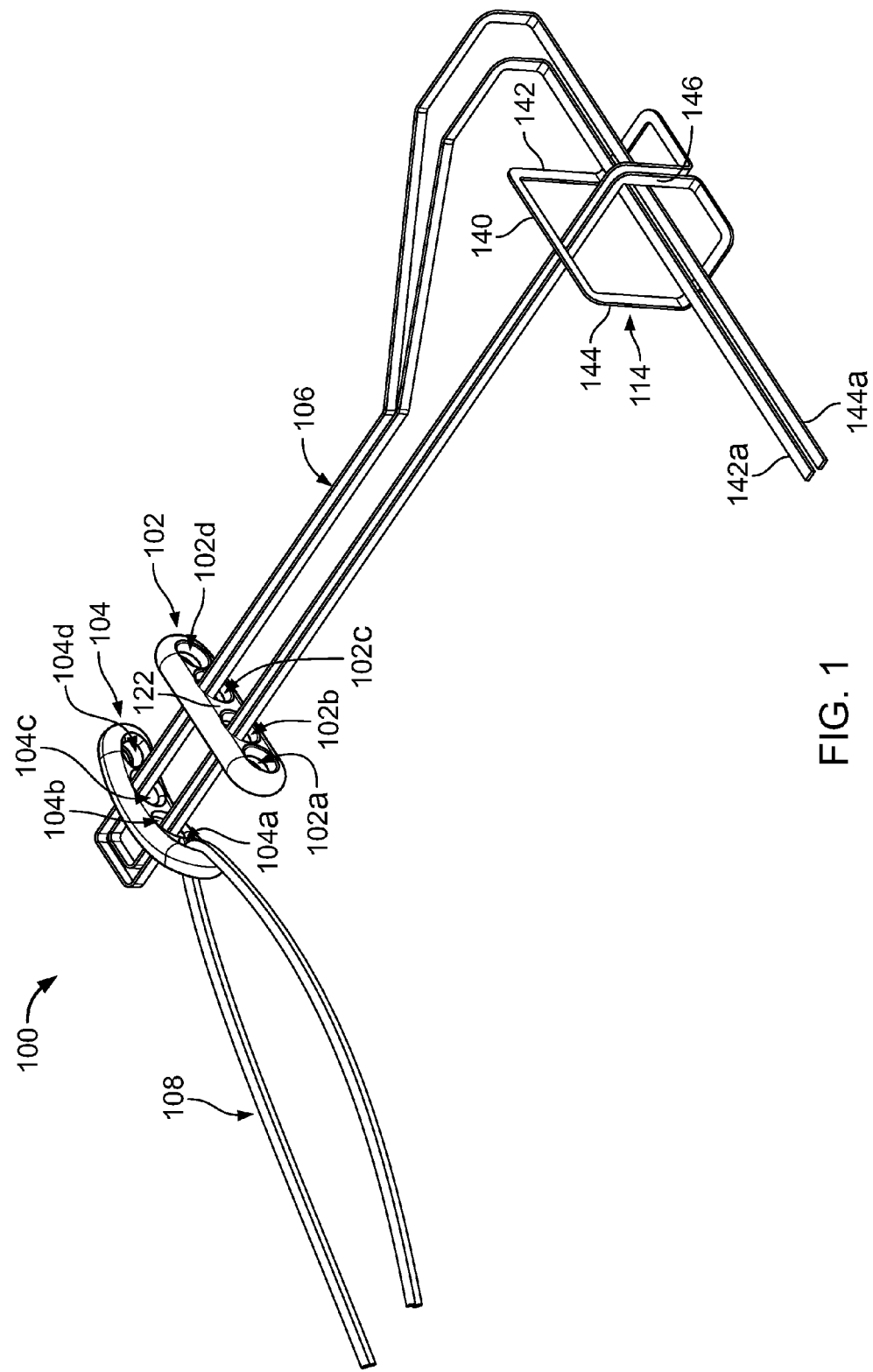
FIG. 1 is a perspective view of a surgical fastening device.

Referring to FIG. 1, a surgical fastening device 100 used, for example, in the repair of complete acromioclavicular joint and coracoclavicular ligament disruption in a patient's shoulder, includes a planar first fastener 102, a curved second fastener 104, a tension suture 106, and a lead suture 108.

Figure 2A:
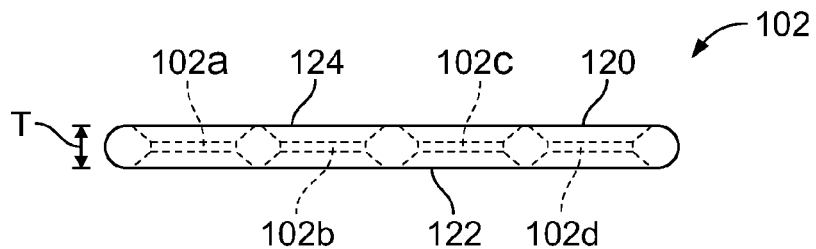
FIGS. 2A and 2B are top and side views of a first fastener of the surgical fastening device.
Figure 2B:
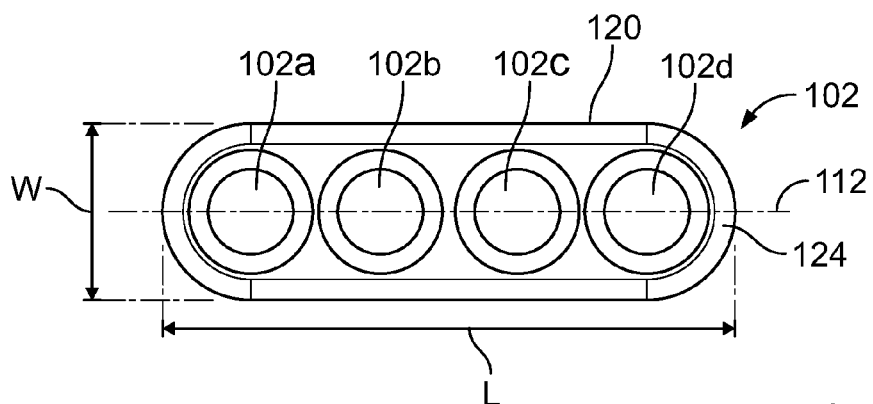
Figure 3A:
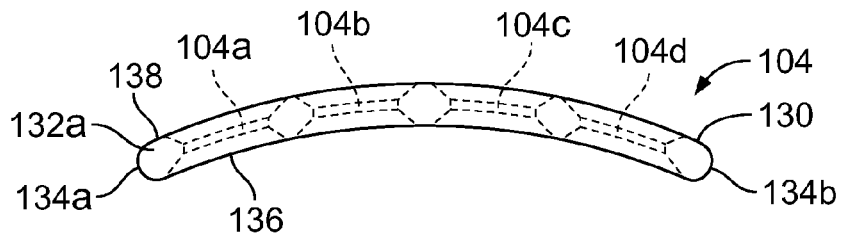
FIGS. 3A and 3B are top and side views of a second fastener of the surgical fastening device.
Figure 3B:
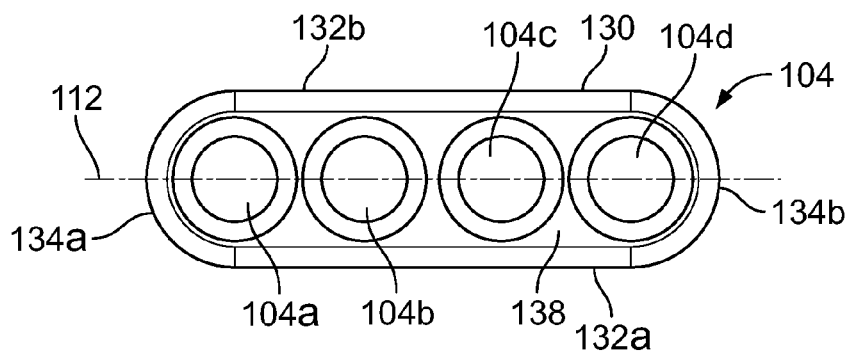

As illustrated in FIGS. 2A and 2B, the first fastener 102 has an elongate, generally rectangular fastener body 120 having a length, $L_1$, along a long axis, 112, of the fastener body of, for example, 14 mm, a width, $W_1$, of, for example, 4 mm, and a thickness, $T_1$, of, for example, 1.5 mm. However, the exact dimensions of the fastener body 120 may be varied. For example, the dimensions may be varied to accommodate a patient or procedure. The first fastener body 120 has a planar profile with a first surface 122 and a second surface 124 that are flat and parallel. The first fastener 102 defines four holes 102a, 102b, 102c, and 102d. Holes 102b and 102c receive suture 106. Alternatively, any combination of holes 102a, 102b, 102c, and 102d may receive suture 106. The second fastener 104, illustrated in FIGS. 3A and 3B, has an elongate, generally rectangular fastener body 130 having, for example, the same overall length, width, and thickness as fastener 102. The second fastener 104 has long edges 132a, 132b, short edges 134a, 134b, a first surface 136 that is concave, and a second surface 138 that is convex such that the fastener body 130 has a curved profile when viewed along a long edge 132a or 132b of the fastener body 130. The second fastener 104 defines four holes 104a, 104b, 104c, and 104d. Holes 104b, 104c receive suture 106, and hole 104a receives suture 108. Alternatively, hole 104d may receive suture 108. Moreover, any combination of holes 104a, 104b, 104c, and 104d may receive suture 106.

Tension suture 106 and lead suture 108 may be made of any common surgical suture material, including, for example, high-strength polyethylene. The tension suture 106 passes through holes 102b, 102c, 104b, and 104c and is tied off with a knot, for example a half-hitch knot 114, that allows the distance between the first fastener 102 and the second fastener 104 to be adjusted by pulling on the ends of the suture 106. The half-hitch knot 114 is formed, for example, by folding the suture 106 roughly in half to form a bight 140 with two suture lengths 142, 144, passing the suture lengths 142, 144 through the bight 140 to form a loop 146, passing the suture lengths 142, 144 through hole 102b, through hole 104b, back through hole 104c and hole 102c, and then through the loop 146. The half-hitch knot 114, also known as a Nice knot, is closed around the suture 106 and moved up to the first fastener 102 by pulling on suture ends 142a, 144a. Further pulling on the suture ends 142a, 144a shortens the length of the suture between the fasteners 102, 104, moving the fasteners closer together. When tightened, the half-hitch knot is preferably located against the first surface 122 of the fastener 102, which corresponds to an outer surface of the fastener in the assembled device 100 (FIG. 1)

Figure 4B:
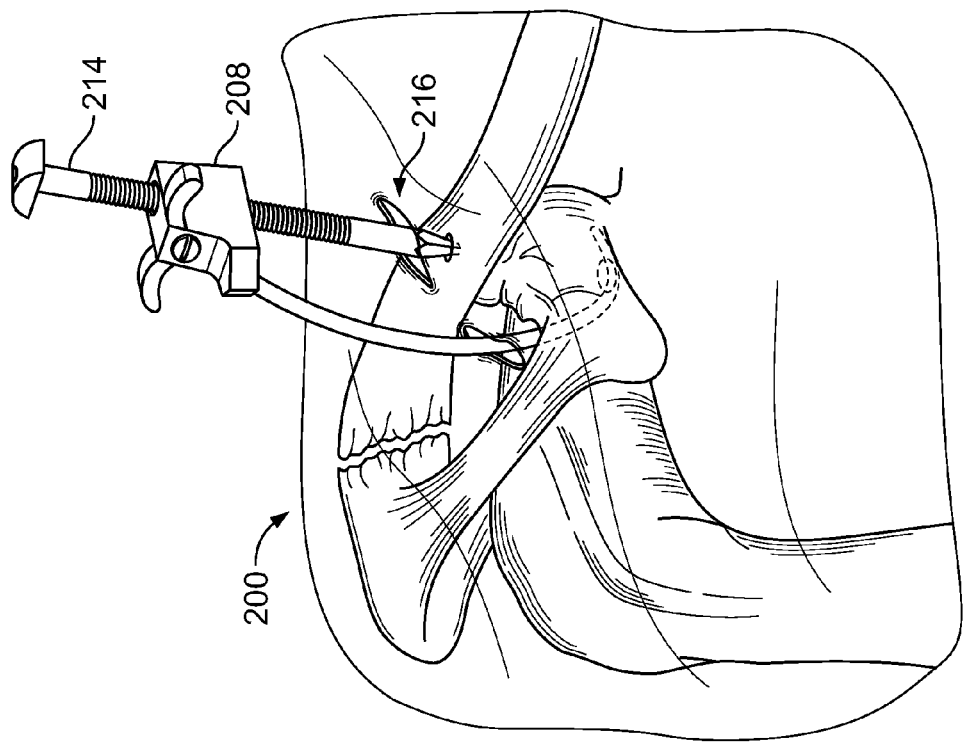
Figure 4A:
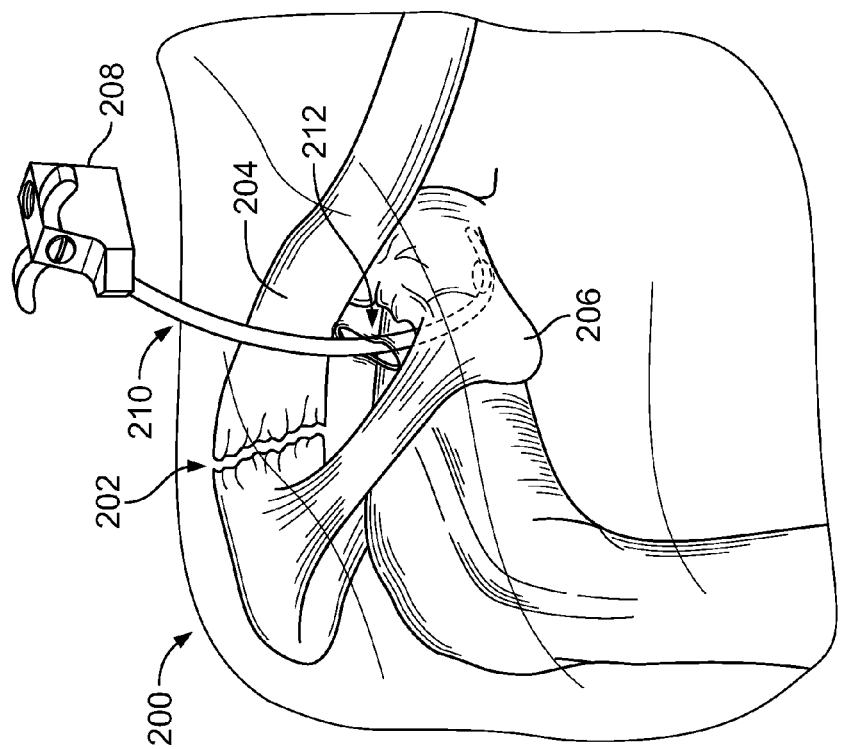

In use, referring to FIGS. 4A-4I, in which a shoulder of patient 200 is illustrated with a disrupted acromioclavicular joint 202, a clavicle 204, and a coracoid process 206, passages are initially drilled through the patient's clavicle 204 and coracoid process 206. In order to establish the passages, the patient needs to be prepared and a drilling guide secured. FIG. 4A shows a clamp 208 of a drilling guide positioned on top of the patient 200's shoulder. The clamp 208 includes a strap 210 used to secure the clamp 208 in place on the top of the patient shoulder. The strap 210 is positioned through a first portal 212 in the front of the patient 200's shoulder, under the patient's scapula, and through a second portal (not shown) in the rear of the patient's shoulder. Next, as shown in FIG. 4B, a first guide tube 214 of the drilling guide is inserted through a hole in clamp 208 and through a third portal 216.

Once the drilling guide is in place, passages in the clavicle 204 and the coracoid process 206 are ready to be formed. FIG. 4C depicts a guide wire 218 (i.e., a drill bit) being inserted through a passage in the first guide tube 214. As the guide wire 218 is moved through the third portal 216 via the first guide tube 214, it encounters the clavicle 204 and is drilled through the clavicle 201 and coracoid process 206. The first guide tube 214 provides the support necessary to drill axially aligned passages through the patient's clavicle 204 and coracoid process 206. In FIG. 4D, the first guide tube 214 is removed from the clamp 208 leaving the guide wire 218 in place. The operator then advances a drill 220 over the guide wire 218 (FIG. 4E) to "over-drill" the passages through the clavicle 204 and the coracoid process 206 to form bone passages each having a diameter that is less than the length, L, of the first and second fasteners 102, 104.

After the aligned passages through the patient's clavicle 204 and coracoid process 206 have been formed, the clamp 208 is removed from the patient's shoulder, as illustrated in FIG. 4F. However, drill 220 is left in place. At this point, the patient's shoulder is prepared for insertion of the surgical fastening device 100. Initially, as shown in FIG. 4G, a fourth portal 222 is created in the patient's shoulder. Next, a shuttling mono-suture 224 is passed through the axially aligned passages in the patient's clavicle 204 and coracoid process 206 via the drill 220.

Figure 4I:
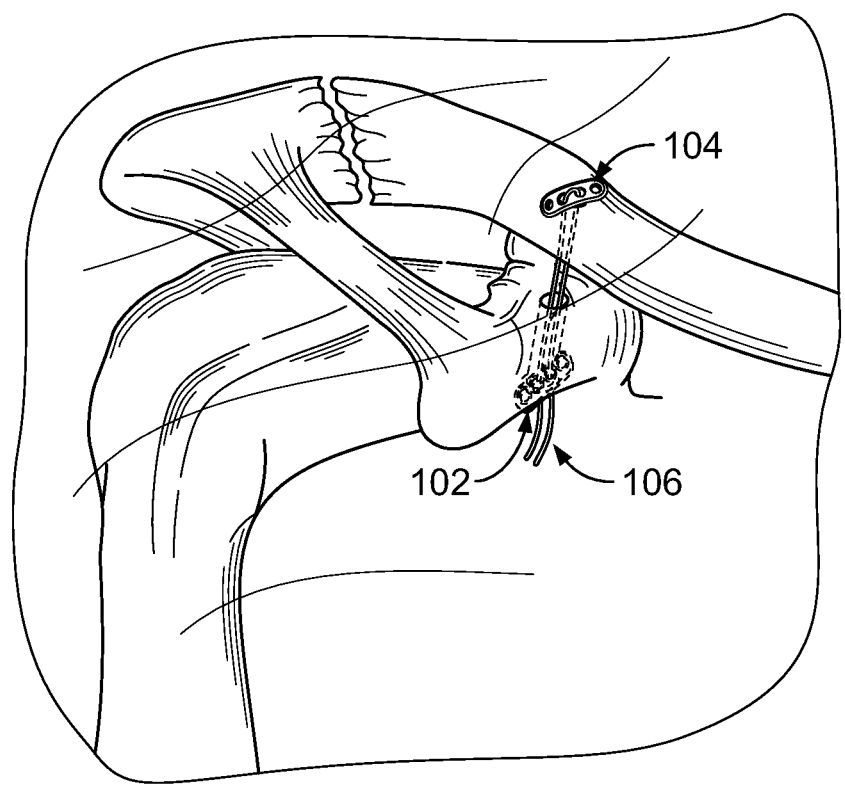

In FIG. 4H, the surgical fastening device 100 is attached to the shuttling mono-suture 224. In particular, the lead suture 108 is passed through a loop 226 in the end of the shuttling mono-suture 224. The shuttling mono-suture 224 is used to pull the surgical fastening device 100 into the patient's shoulder through the fourth portal 222. The shuttling mono-suture 224 pulls the lead suture 108, second fastener 104, and tension suture 106 up through the axially aligned passages in the patient's clavicle 204 and coracoid process 206, with the first fastener 102 and the half-hitch knot 114 positioned below the coracoid process 206 (FIG. 4I). Positioning the knot 114 below the coracoid process 206 rather than above the clavicle 204 lessons any visible protrusion of the surgical fastener on the top of the patient's shoulder and decreases the likelihood of infection.

During passage of the second fastener 104 through the passages in the patient's clavicle 204 and coracoid process 206, a long axis 112 (FIG. 3B) of the second fastener 104 is aligned with a longitudinal axis 228 of the passages. After exiting through the passage in the clavicle 204, the operator flips the second fastener 104 using the suture 108. The second fastener 104 is seated on the top surface of the clavicle 204 with the long axis 112 of the second fastener 104 roughly transverse to an axis 230 of the clavicle 204, and the concave surface 136 abutting the surface of the clavicle 204.

With the first fastener 102 positioned below the coracoid process 206, the second fastener 104 positioned above the clavicle 204, and the suture 106 extending through the passages in the coracoid process 206 and clavicle 204, the coracoclavicular is manually reduced through application of external pressure on the patient's shoulder to reduce the distance between the patient's coracoid process and clavicle to re-approximate the bones, tendons, and ligaments back to their anatomical locations.

Next, the operator pulls on the ends 142a, 144a of the suture 106 to shorten the length of the suture 106 between the fasteners 102, 104 such that the distance between the fasteners 102, 104 conforms to the reduction in the coracoclavicular, with the surface 120 of the first fastener 102 up against the surface of the coracoid process 206. The operator then further reduces the coracoclavicular if desired. After the coracoclavicular is reduced to the preferred distance, a surgical knot is tied behind the half-hitch knot 114. The shuttling mono-suture 224 is removed from the patient 200. Finally, the first portal 212, the second portal (not shown), the third portal 216, and the fourth portal 222 are stitched closed.

The passages formed in the coracoid process 206 and the clavicle 204 are sized to allow passage of the second fastener 104. Relatedly, the curvature of the second fastener 104 is selected such that the second fastener 104 can pass through the passages and to match the size and curvature of the patient's clavicle 204. For the same length fastener, as the curvature of the second fastener 104 increases, the diameter of the passages necessarily increases to allow the second fastener 104 to pass through the passages. However, it is generally better to keep the diameter of the passages formed in the coracoid process 206 and the clavicle 204 as small as possible to maintain the integrity of the coracoid process 206 and the clavicle 204. Therefore, depending on the size of the clavicle 204, there can be a trade-off between the diameter of the passages and the extent to which the curvature of the second fastener 104 matches that of the clavicle 204. To accommodate different sized patients, a kit of surgical fastening devices 100 can be provided to the surgeon, with each surgical fastening device 100 including a second member having a different curvature or varying in other different overall dimensions.

Alternative fasteners 304, 306, 308, and 310, illustrated in FIGS. 5A-5D, are similar in construction to the first fastener 102, with the addition of suture grooves that allow the fastener to lie flat against a bone surface. For example, the groove extends from a hole in the fastener that receives the suture 106 and the suture ends 142a, 144a lie within the groove such that the suture does not protrude beyond the surface of the fastener. Each of the fasteners 304, 306, 308, and 310 is formed with a different configuration of suture grooves. The fastener 304 includes a suture groove 320 on the surface 120 and a suture groove 322 on the surface 122 at an opposite end of the fastener. The fastener 306 includes a single suture groove 324 on the surface 120. The fastener 308 includes a suture groove 326 on the surface 120 and an opposite suture groove 328 on the surface 120. The fastener 310 includes a single suture groove 330 on the surface 120, with the holes of the fastener 310 being offset, such that a hole 332 from which the groove 330 extends is further from the end 134b of the fastener than a hole 334 at the opposite end 134a of the fastener. The curved second fastener 104 can similarly be provided with one or more grooves.

The first fastener 102 and the second fastener 104 can be made from a biocompatible material, such as titanium.

Figure 5A:
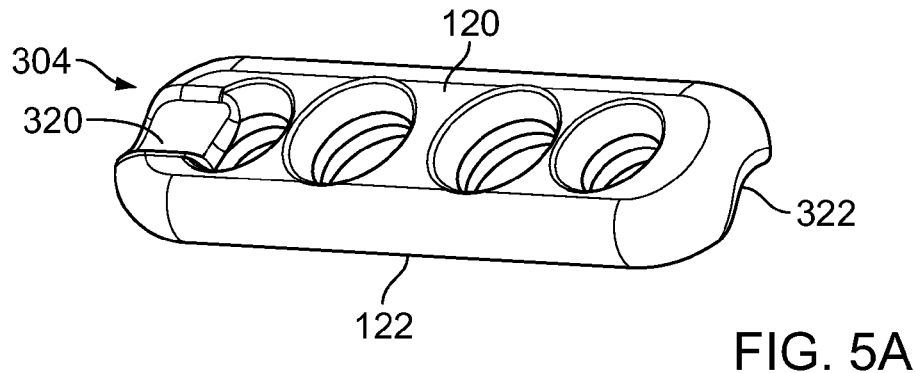
FIGS. 5A-5D are perspective views of alternative embodiments of a fastener.
Figure 5B:
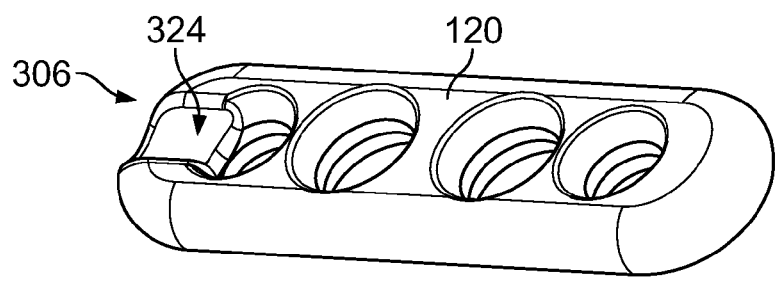
Figure 5C:
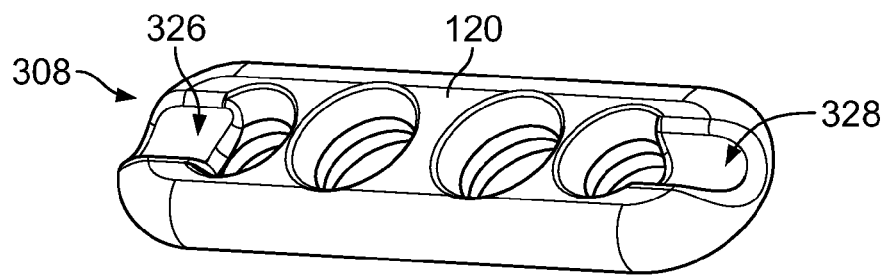
Figure 5D:
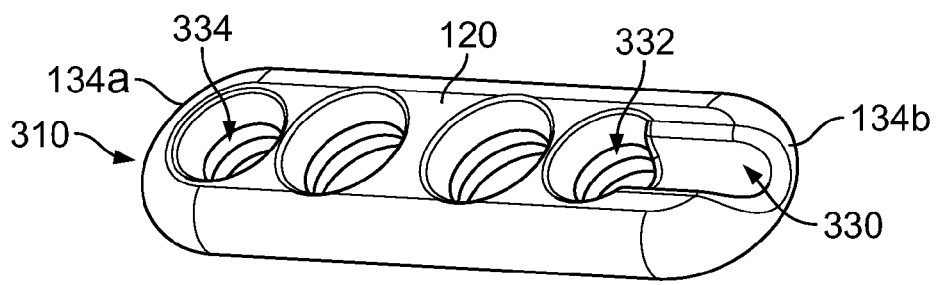
Figure 5E:
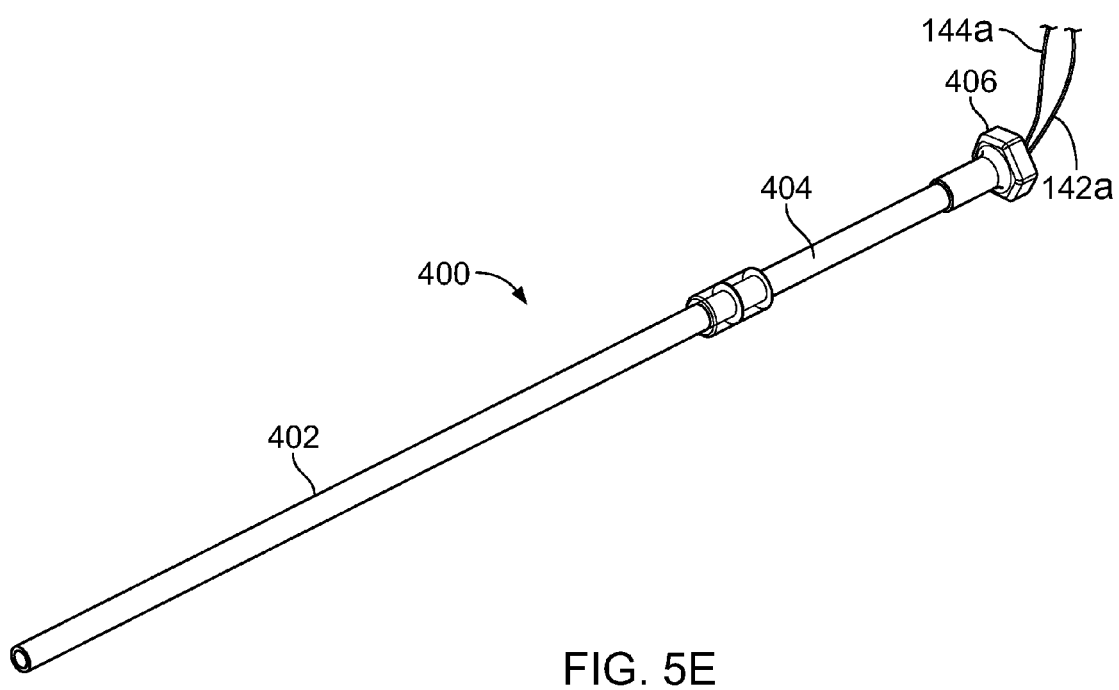
FIG. 5E is a perspective view of a delivery device for a surgical fastening device.

Though the procedure described in FIGS. 2A-2I regards an insertion of the surgical fastening system 100 from the bottom-up (i.e., through the patient's coracoid process and then through the patient's clavicle), it is possible to perform the procedure from the top-down (i.e., through the patient's clavicle and then the patient's coracoid process). In a top-down procedure, the first fastener 102 of the fastening device 100 would be passed through a passage in a patient's clavicle and coracoid process such that the fastening device 100 is ultimately oriented in the patient's shoulder in the same manner as the bottom-up procedure. When a surgical fastening system is inserted from the top-down, an insertion device 400, such as illustrated in FIG. 5E, can be used to protect the surgical fastening device from fraying. The insertion device 400 includes a first hollow tube 402, a second hollow tube 404, and a handle 406 having a through bore for receiving the surgical fastening device 100 with the suture ends 142a, 144a extending out the handle through bore. The second tube 404 is slidably received within the first tube 402 to adjust the length of the insertion device 400.

In use, with the fastening device 100 received in the insertion device 400 and the first and second tubes 402, 404 in an extended position, the operator advances the insertion device 400 through the passages drilled in the patient's clavicle and coracoid process from the top-down to position the first fastener 102 against the surface of the coracoid process. Once positioned, the operator retracts the second tube 404 into the first tube 402 to release the surgical fastening device 100. In other words, while holding the first tube 402, the operator presses on the handle 406, causing the second tube 404 to retract into the first tube 402. The operator then removes the insertion device 400.

Figure 6B:
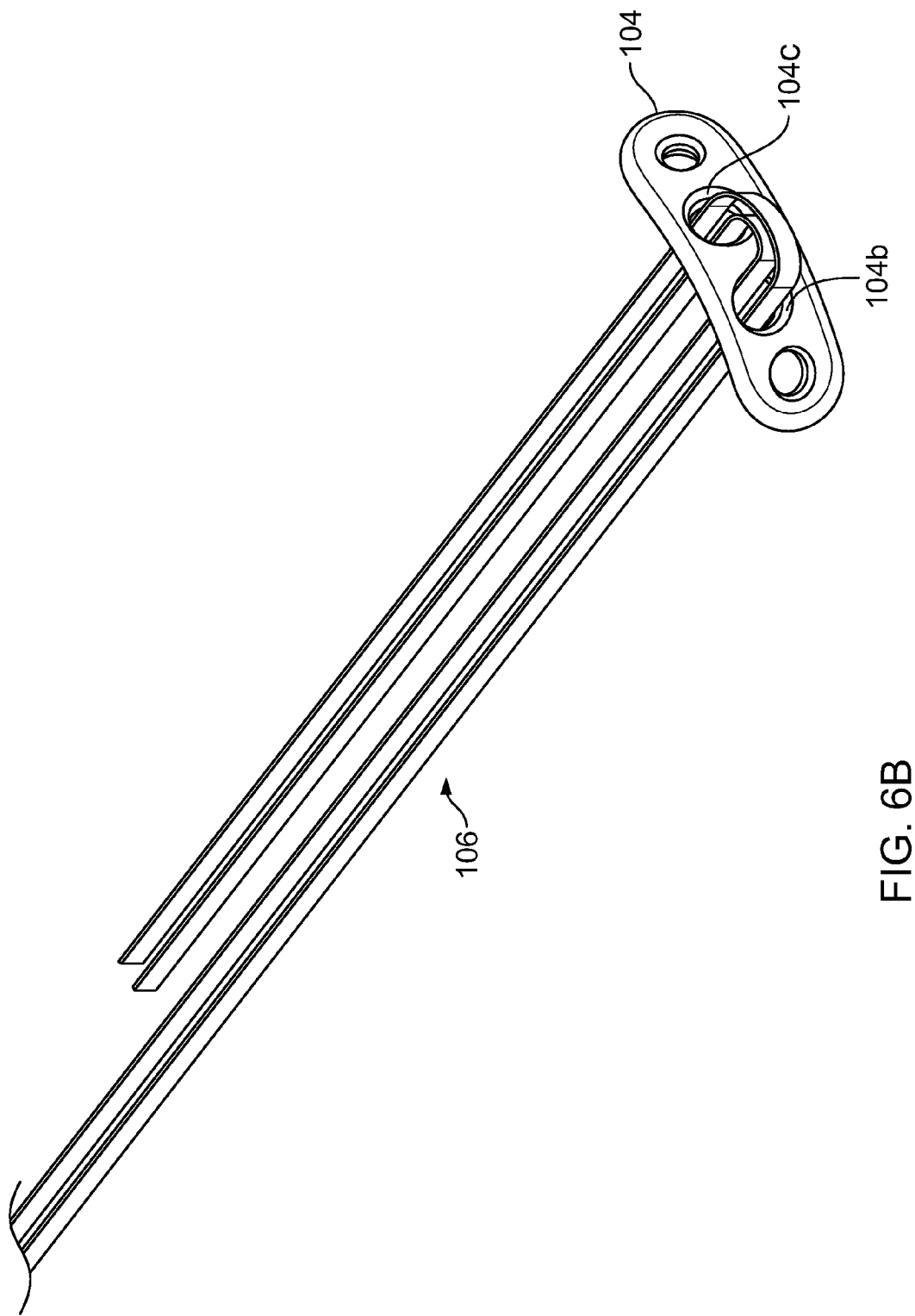

The surgical fastening device 100 may be used in other surgical procedures as well. For example, the surgical fastening device 100 may be used in a bone block procedure, such as a Latarjet procedure, to repair a patient's glenoid. Referring to FIGS. 6A-6E, in which a glenoid of patient 600 is illustrated, a portion of the patient's coracoid process 602 has been removed and positioned in a standing position on the neck of the patient's glenoid 604. As shown in FIG. 6A, a passage 606 is drilled through the patient's removed coracoid process 602 and glenoid 604.

Figure 6C:
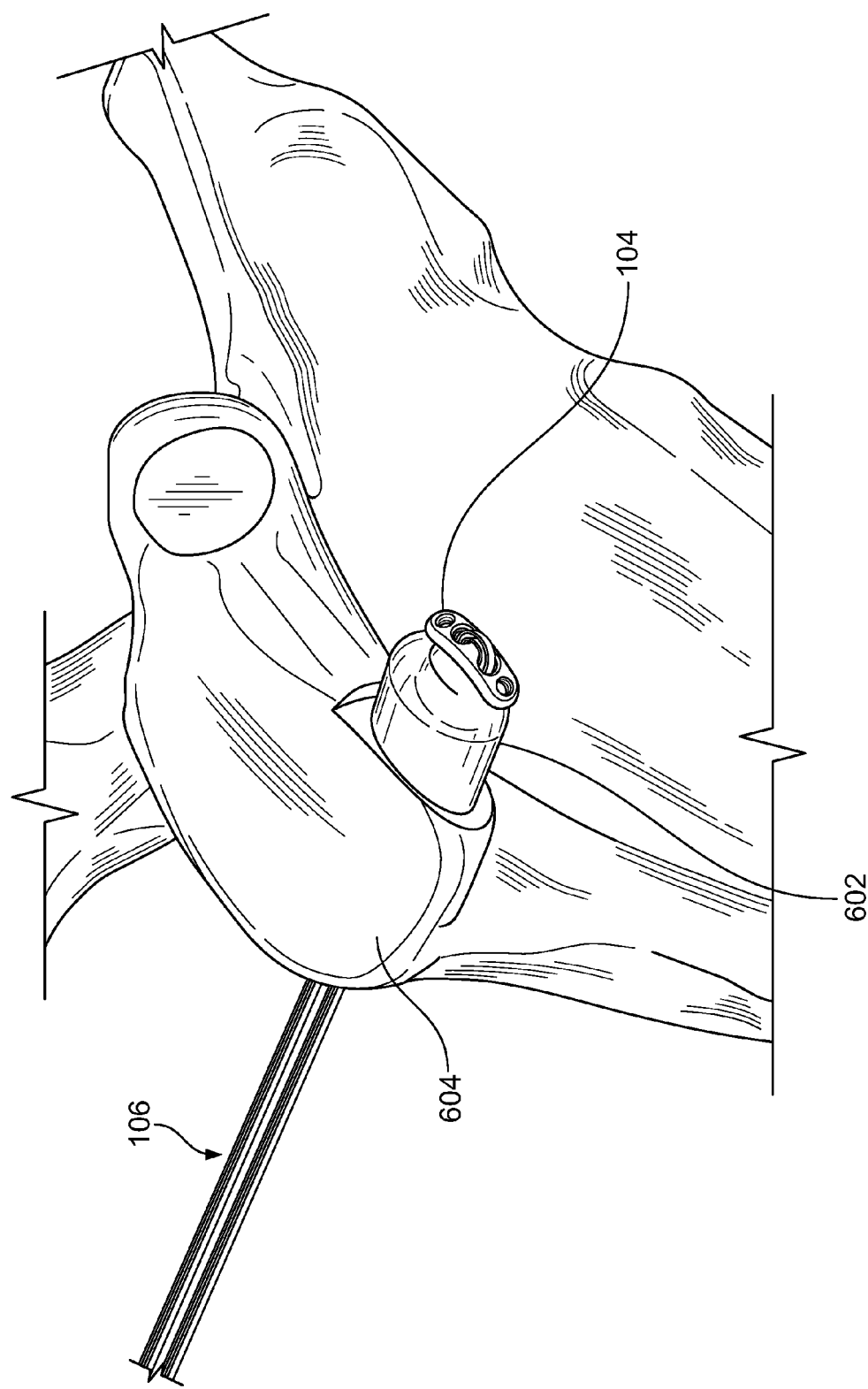
Figure 6D:
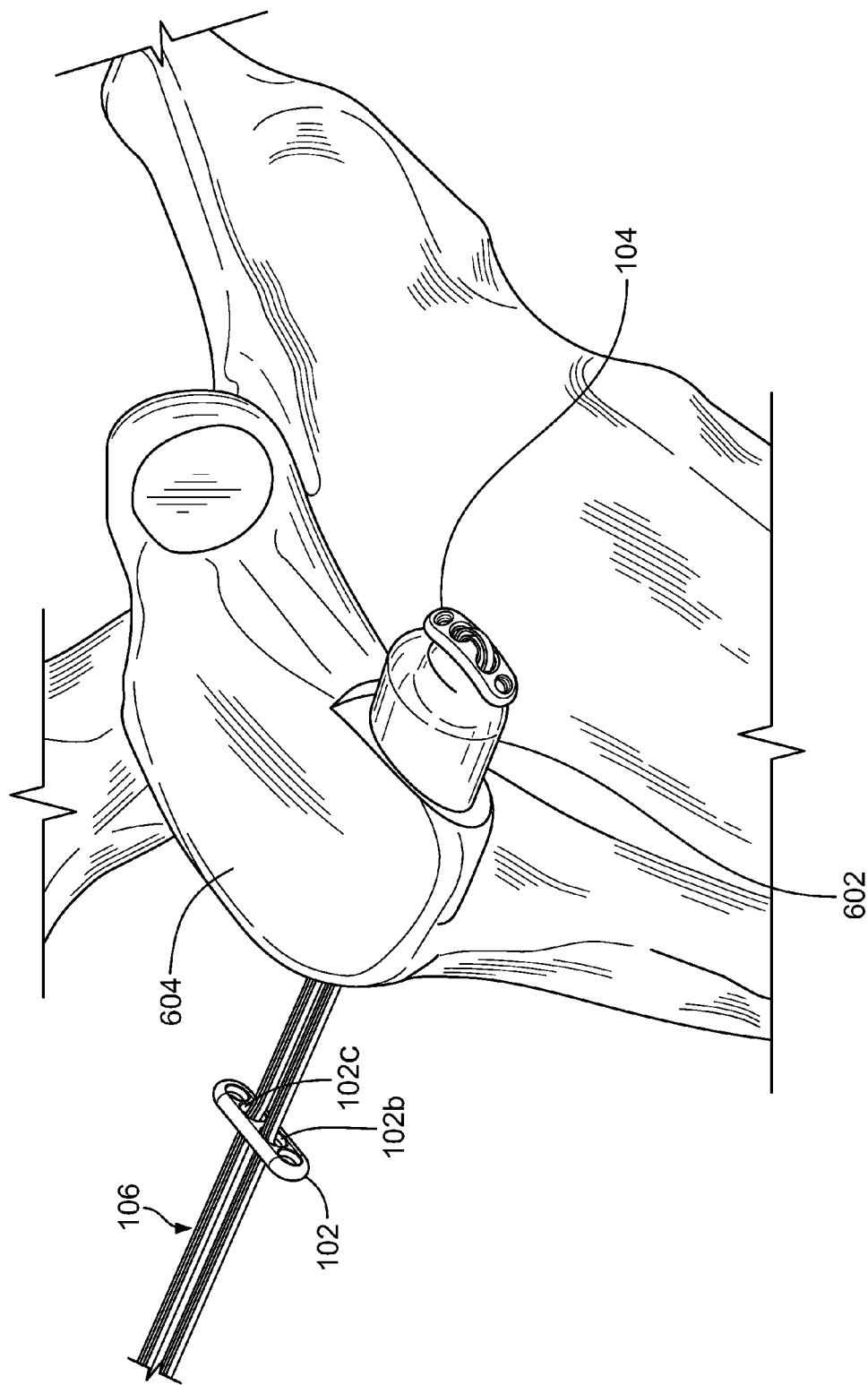

In preparation for installing the surgical fastening device 100, a length of suture 106 is folded in half. As shown in FIG. 6B, the closed end of the folded suture is passed through holes 104b and 104c of the second fastener 104. Having been passed through the second fastener 104, the suture 106 is passed through the passage 606, as shown in FIG. 6C. Both ends of the suture 106 are pulled posteriorly and exteriorized until the concave surface of the second fastener 104 is positioned against the cortical tip of the patient's coracoid process 602. After the second fastener 104 is positioned, the first fastener 102 is loaded onto the suture as shown in FIG. 6D. In particular, the closed end of the suture 106 is passed through hole 102b and the open end of the suture 106 is passed through hole 102c.

Figure 6E:
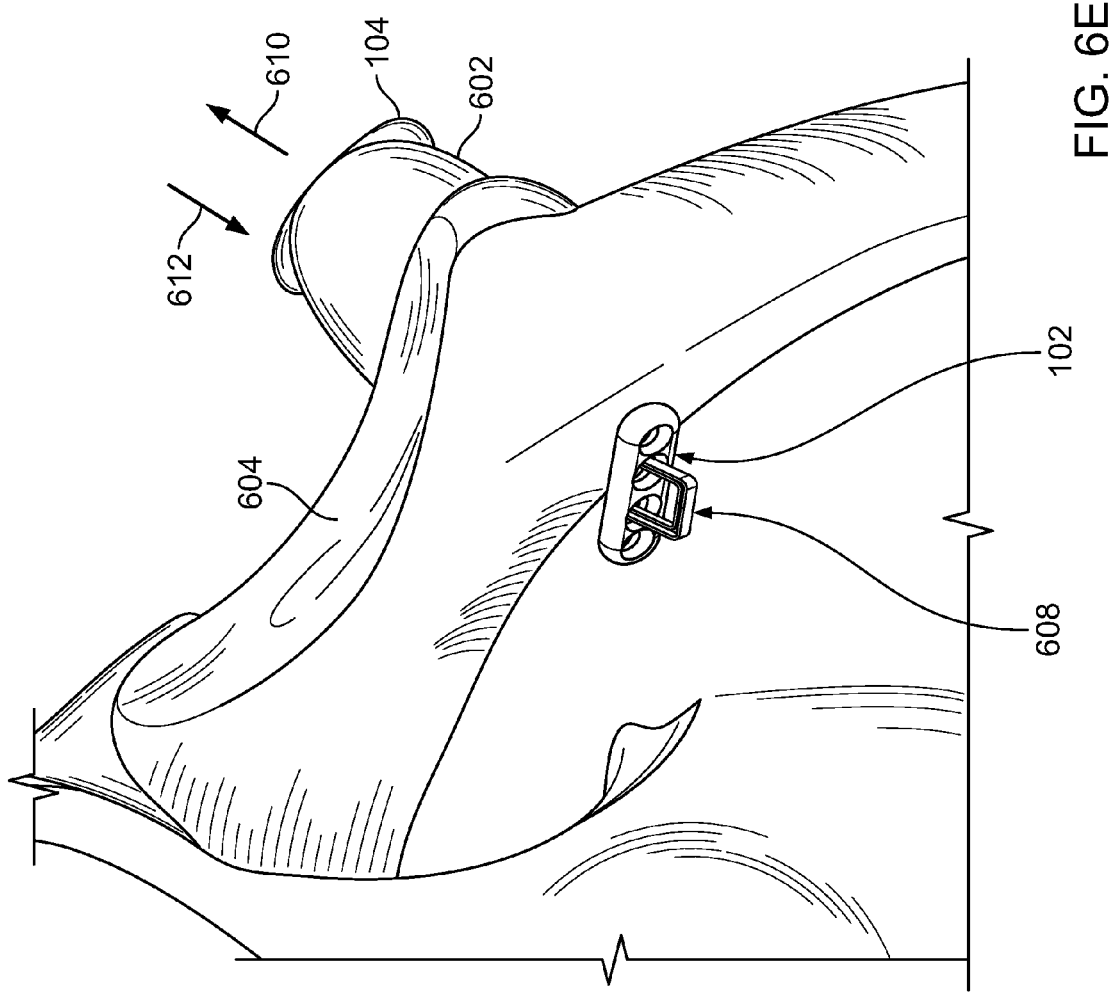

Once loaded onto suture 106, the first fastener 102 is slid up the suture until it is positioned against the posterior surface of the patient's glenoid 604. Next, a sliding knot 608 is tied with the open and closed ends of the suture 106 and cinched against the first fastener 102, as shown in FIG. 6E. As the sliding knot is cinched, the tension of suture 106 causes the first fastener 102 to apply pressure in a first direction 610 to the posterior of the patient's glenoid 604 and causes the second fastener 104 to apply pressure in an opposite direction 612 to the removed coracoid process 602 such that the removed coracoid process 602 is compressed against the neck of the patient's glenoid 604. A knot pusher (not shown) may be used to increase tension in the suture 106. Once the sliding knot 608 has been tied off, the pressure created by the surgical fastening device 100 between the removed coracoid process 602 and the neck of the patient's glenoid 604 will cause the two bones to fuse during the healing process.

There are number of possible variations to the Latarjet procedure described above with regard to FIGS. 6A-6E. For example, the surgical fastening device 100 may be installed from the opposite direction. In particular, the closed end of the folded suture 106 is passed through holes 102b and 102c of the first fastener 102. The folded suture 106 is then passed through the passage 606 in the reverse direction as described above with regard to FIGS. 6A-6E (i.e., from the posterior of the patient's glenoid 604 to the cortical tip of the removed coracoid process 604). After positioning the first fastener 102 against the posterior of the patient's glenoid 604, the second fastener 104 is loaded onto the suture 106 by passing the closed end of the suture 106 through hole 104b and passing the open end of the suture 106 through hole 104c. Once the concave surface of the second fastener 104 has been positioned against the cortical tip of the removed coracoid process 604, the sliding knot 608 is cinched against the convex surface of the removed coracoid process 604.

Figure 7A:
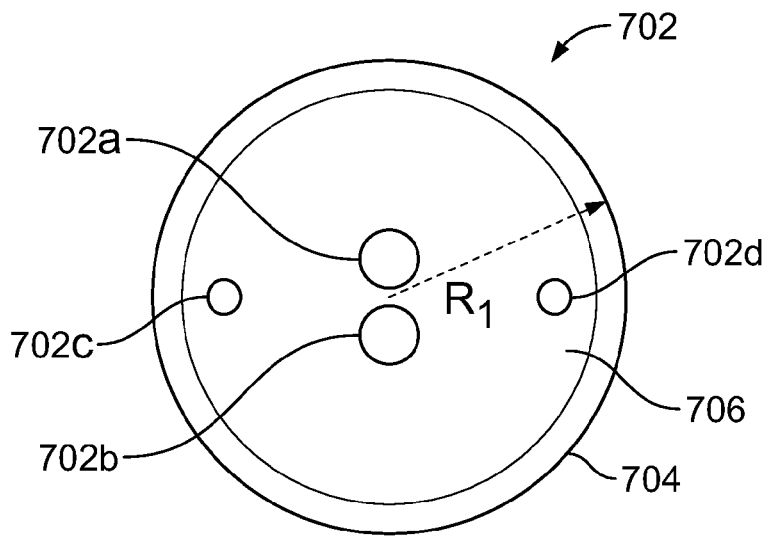
FIGS. 7A-7C are views of another fastener.
Figure 7B:
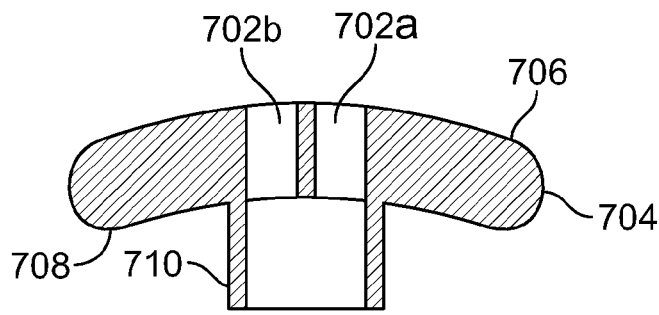
Figure 7C:
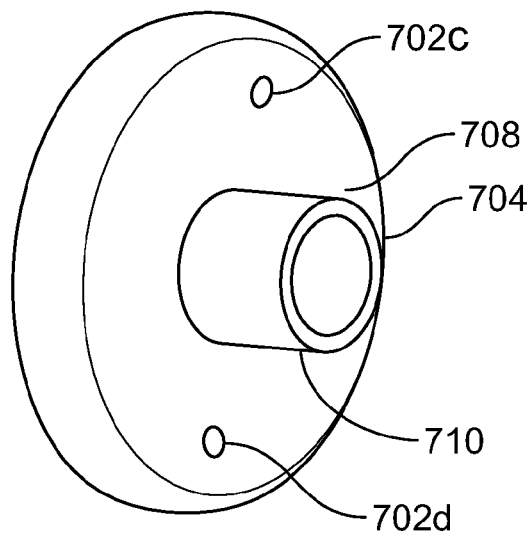

Variations of the fastening device 100 may be used in the Latarjet procedure, as illustrated in FIGS. 7A-7C. For example, the shape of the second fastener 104 may be changed to accommodate the cortical tip of the patient's coracoid process. As shown in FIG. 7A, a second fastener 702 may be formed with a generally circular body 704 having a radius $R_1$ across a first surface 706 of the fastener body of, for example, 7 mm. However, the radius R1 across a first surface 706 may be varied. For example, the radius may be varied to accommodate a patient or procedure. The first surface 706 of the second fastener 702 is convex and a second surface 708 is concave such that the second fastener 702 has a bowl-shaped profile. The second fastener 702 defines two large holes 702a and 702b and two small holes 702c and 702d. The two large holes 702a and 702b include a neck 710 that protrudes from the concave second surface 708. Fastener 702 is used similar to fastener 104 in the Latarjet procedure described above, with the suture passed through the large holes 702a and 702b. When the concave second surface 708 of the second fastener 702 is positioned against the cortical tip of the patient's coracoid process 602, the neck 710 fits inside of the passage 606 and protects the suture 106 from the sharp edges of the passage 606. Supplemental sutures may be passed through the two small holes 702c and 702d in order to assist in positioning and securing the second fastener 702 inside the patient. Alternative implementations of fastener 702 eliminate the neck 710.

Figure 8:
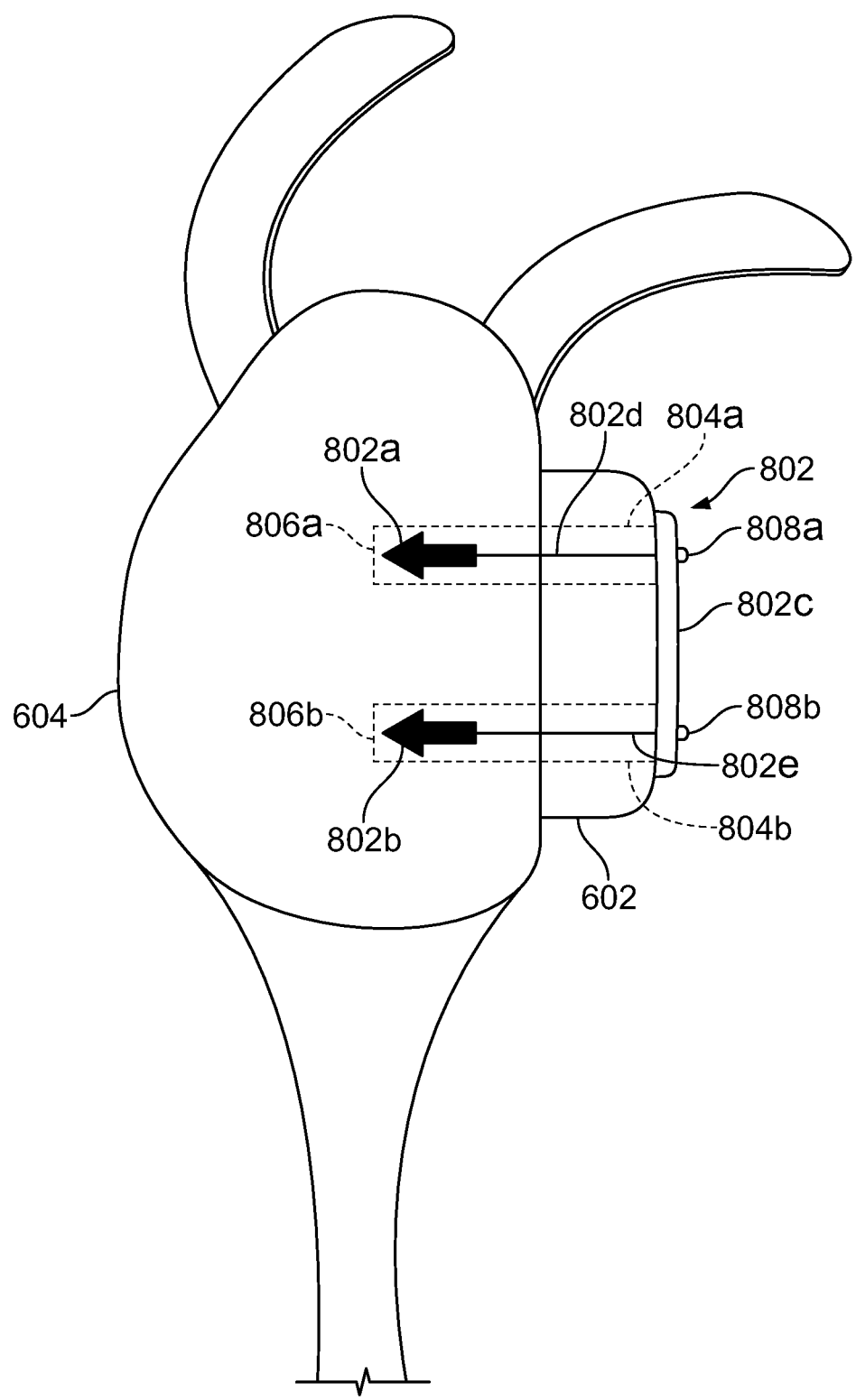
FIG. 8 illustrates another surgical fastening device.

Referring to FIG. 8, instead of positioning the removed coracoid process 602 in a standing position against the neck of the patient's glenoid 604, as described above with regard to FIGS. 6A-6E, the removed coracoid process 602 may be positioned on its side such that a greater surface area of the removed coracoid process 602 contacts the neck of the patient's glenoid 604. As shown in FIG. 8, when the coracoid process 602 is positioned on its side, two passages 804a and 804b are drilled through the patient's removed coracoid process 602 and glenoid 604 and a fastening device 802 is employed with the two passages 804a and 804b to stabilize the removed coracoid process 602 during the healing process.

The surgical fastening device 802 includes a fastener 802c, which may be the same as fastener 104 and two bone anchors 802a and 802b. Each bone anchor 802a and 802b has two strands of suture 802d and 802e attached to the respective bone anchor 802a and 802b. Each of the two bone anchors 802a and 802b are either screwed or pounded into the patient's glenoid 604, such that the bone anchors 802a and 802b each sit in a passage 806a and 806b, respectively, with the strands of suture 802d and 802e protruding from the two passages. Once the bone anchors 802a and 802b are positioned in the passages 806a and 806b, the strands of suture 802d and 802e attached to each of the bone anchors 802a and 802b are passed through respective passages 804a and 804b in the removed coracoid process 602. The second fastener 104 is loaded onto the sutures 802d and 802e attached to each of the bone anchors 802a and 802b by passing the sutures 802d and 802e through respective holes in fastener 802c. In particular, strands 802d pass through a hole like hole 104b and strands 802e pass through a hole like hole 104. Once the concave surface of the second fastener 802 has been positioned against the coracoid process 602, a sliding knot 808a and 808b is formed in each of the strands 802d and 802e, and cinched against the convex surface of the fastener 802c.

Though this procedure may be performed with the surgical fastening device 802 as described, the procedure may be performed with the surgical fastening device 100 (and passages that extend fully through the glenoid 604) in a manner similar to the procedure described with regard to FIGS. 6A-6E.

Figure 9A:
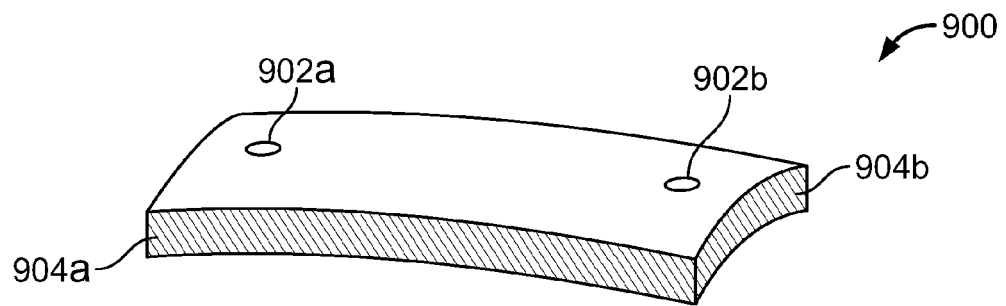
FIGS. 9A and 9B illustrate another fastener.
Figure 9B:
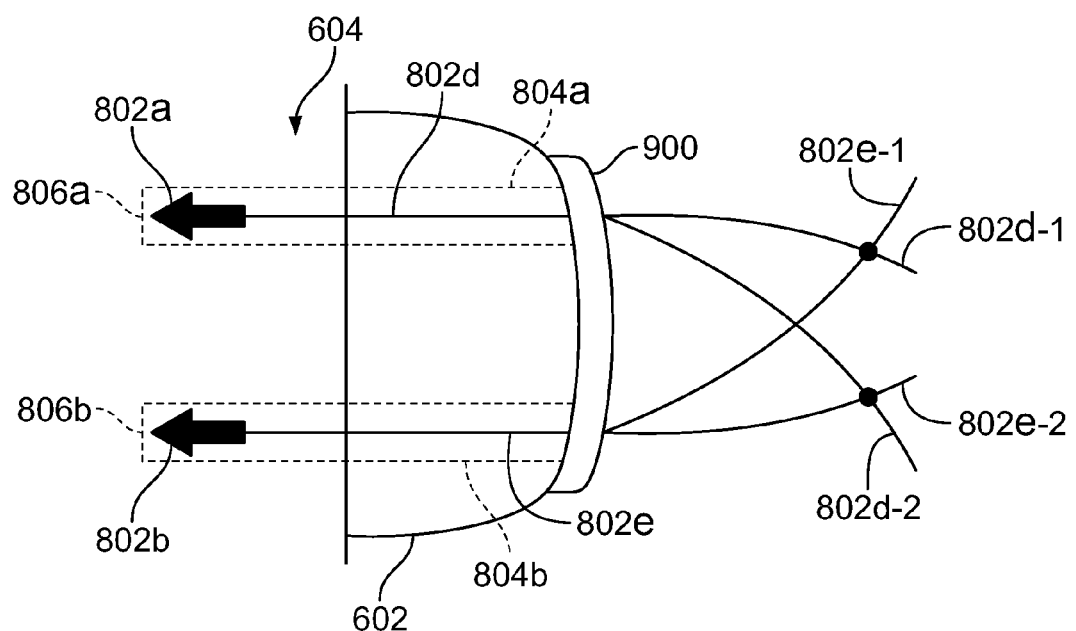

Referring to FIGS. 9A and 9B, a nice knot may be used in conjunction with an alternative fastener 900 that is designed to be positioned flush against the surface of the coracoid process 602. As shown in FIG. 9A, the fastener 900 has a similar construction to the second fastener 104, however the fastener 900 only defines two holes 902a and 902b. Moreover, in addition to being convex such that the fastener body has a curved profile when viewed along a long edge 904a (like fastener 104), the body of fastener 900 has a curved profile when viewed along a short edge 904b. These curvatures of the fastener 900 are defined such that the concave surface of the fastener 900 can be positioned substantially flush against the surface of coracoid process 602.

The fastener 900 is loaded onto the sutures 802d and 802b attached to each of the bone anchors 802a and 802b after they have been secured in the patient's glenoid 604. In particular, the sutures 802d attached to bone anchor 802a are passed through hole 902a and the sutures 802e attached to bone anchor 802b are passed through hole 902b. The concave surface of the fastener 900 is positioned against the surface of coracoid process 602. After the fastener 900 has been positioned, a surgeon's knot is tied with the sutures attached to the bone anchors 802a and 802b. Various surgeon's knots, including, for example, the half-hitch knot 114 described above with regard to FIG. 1, may be used to tie the sutures 802d and 802e.

Though the surgical fastening device 802 has been described as part of the Latarjet procedure using a patient's coracoid process, the surgical fastening device 802 may be used as part of a bone block procedure with a bone implant from the patient's iliac crest or harvested from a cadaver. Generally, the bone implant is cut with dimensions such that a surface of the bone implant that contacts the patient's glenoid is approximately 7 mm by 25 mm and such that the bone implant has a height 7 mm above the patient's glenoid. However, the dimensions of the bone implant may be adjusted in proportion to the patient's glenoid. Regardless of size, the bone implant will be installed in substantially the same manner as described above with regard to FIGS. 8 and 9B.

A number of embodiments of the invention have been described. Nevertheless, it will be understood that various modifications may be made without departing from the spirit and scope of the invention. For example, the surgical fastening system 100 could be scaled for use in a patient's foot, hand, or wrist. Accordingly, other embodiments are within the scope of the following claims.

What is claimed is:

1. A method of treating an acromioclavicular (AC) joint injury, comprising:
    forming axially aligned passages through a patient's clavicle and coracoid process;
    passing a fastener having a concave surface through the passages;
    positioning the concave surface of the fastener against a top surface of the patient's clavicle with a long axis of the fastener extending perpendicular to a long axis of the clavicle;
    positioning a fastener having a planar profile below the patient's coracoid process; and
    adjusting a suture that couples the fasteners to decrease a distance between the fasteners.

2. The method of claim 1 wherein the suture includes a half-hitch knot and adjusting the suture includes pulling on ends of the suture.

3. The method of claim 1 further comprising tying a knot in the suture such that the knot is against an outer surface of the planar fastener.

4. The method of claim 1 wherein passing the fastener having a concave surface through the passages comprises pulling on a second suture attached to the concave fastener.

5. A method comprising:
    positioning a bone graft in contact with a patient's glenoid;
    forming at least one axially aligned passage through the patient's glenoid and the bone graft;
    passing a first portion of a suture through the passage, wherein a second portion of the suture is coupled to a first fastener;
    positioning a surface of the first fastener against a surface of the bone graft opposite a surface of the bone graft in contact with the patient's glenoid;
    positioning a surface of a second fastener against a surface of the glenoid opposite a surface of the glenoid in contact with the bone graft, wherein the second fastener is coupled to a third portion of the suture; and
    adjusting the suture such that the first fastener and the second fastener apply pressure between the bone graft and the patient's glenoid;
    wherein the first fastener and the second fastener are not passed through the passage.

6. The method of claim 5 wherein the bone graft is at least a portion of the patient's coracoid process.

7. The method of claim 6 wherein positioning the portion of the patient's coracoid process in contact with the patient's glenoid includes positioning the portion of the patient's coracoid process upright such that a longest dimension of the patient's coracoid process is oriented substantially orthogonal to the surface of the glenoid in contact with the patient's coracoid process.

8. The method of claim 6 wherein positioning the portion of the patient's coracoid process in contact with the patient's glenoid includes positioning the portion of the patient's coracoid process laying down such that a longest dimension of the patient's coracoid process is oriented substantially parallel to the surface of the glenoid in contact with the patient's coracoid process.

9. The method of claim 5 wherein the first fastener and the second fastener each have a planar profile.

10. The method of claim 5 wherein the first fastener has a planar profile and the second fastener has a curvature along a longitudinal axis of the second fastener, a length of the second fastener along the longitudinal axis being greater than a width of the second fastener along a lateral axis of the second fastener.

11. The method of claim 10 wherein the second fastener further has a curvature along a lateral axis of the second fastener.

12. The method of claim 5 wherein:
    the second fastener has a circular body with a convex surface and a corresponding, opposite concave surface; and
    the second fastener defines two holes for receiving suture and a neck protruding from the concave surface that surrounds the two holes, an outer diameter of the neck being less than or equal to a diameter of the passage through the bone graft.

13. The method of claim 5, further comprising folding the suture upon itself prior to passing through the passage.

14. The method of claim 13, wherein the folded suture includes a closed end and wherein coupling a second portion of the suture to the first fastener comprises passing the folded end of the suture through two holes of the first fastener.

15. The method of claim 5, wherein the bone graft is not laterally constrained by the patient's anatomy.

16. The method of claim 5, wherein the bone graft is maintained in place by constraint consisting essentially of the pressure created by the first and second fasteners between the bone graft and the patient's glenoid.

17. The method of claim 5, wherein the bone graft is not positioned into contact with the glenoid within a cavity formed within the glenoid.

18. A method comprising:
positioning a bone graft in contact with a patient's glenoid;
forming two axially aligned passages through the patient's glenoid and the bone graft;
inserting a bone anchor into each of the two passages in the patient's glenoid, wherein each bone anchor includes a length of suture that protrudes from the patient's glenoid when the bone anchor is inserted;
passing a first portion of suture attached to a first of the bone anchors through a first passage in the bone graft after insertion of the first bone anchor into the patient's glenoid;
passing a second portion of suture attached to a second of the bone anchors through a second passage in the bone graft after insertion of the second bone anchor into the patient's glenoid;
positioning a surface of a first fastener against an outer surface of the bone graft opposite a surface of the glenoid in contact with the bone graft, wherein the first fastener is coupled to the first portion of suture and the second portion of suture and wherein the first fastener does not extend beneath the outer surface of the bone graft; and
adjusting the suture such that the first fastener applies pressure between the bone graft and the patient's glenoid.

19. The method of claim 18 wherein the first fastener has a curvature along a longitudinal axis of the first fastener and a curvature along a lateral axis of the first fastener, a length of the first fastener along the longitudinal axis being greater than a width of the first fastener along a lateral axis of the first fastener.

20. The method of claim 18 wherein:
a third portion of suture is attached to the first bone anchor and the first fastener;
a fourth portion of suture is attached to the second bone anchor and the first fastener; and
the first, second, third, and fourth portions of suture are tied together to form a half-hitch knot.

* * * * *